United States Patent
Wolgen

(10) Patent No.: US 8,334,265 B2
(45) Date of Patent: Dec. 18, 2012

(54) METHOD OF TREATMENT OF PHOTODERMATOSES

(75) Inventor: Philippe Wolgen, Melbourne (AU)

(73) Assignee: Clinuvel Pharmaceuticals Limited, Melbourne, Victoria (AU)

( * ) Notice: Subject to any disclaimer, the term of this patent is extended or adjusted under 35 U.S.C. 154(b) by 558 days.

(21) Appl. No.: 12/438,990

(22) PCT Filed: Aug. 31, 2007

(86) PCT No.: PCT/AU2007/001276
§ 371 (c)(1),
(2), (4) Date: Jul. 21, 2009

(87) PCT Pub. No.: WO2008/025094
PCT Pub. Date: Mar. 6, 2008

(65) Prior Publication Data
US 2010/0120668 A1   May 13, 2010

(30) Foreign Application Priority Data

Aug. 31, 2006  (AU) ................ 2006904745
Feb. 21, 2007  (AU) ................ 2007900862

(51) Int. Cl.
*A61K 38/08* (2006.01)
*A61K 38/10* (2006.01)
*A61K 38/34* (2006.01)
*A61P 17/00* (2006.01)

(52) U.S. Cl. ...................... 514/18.6; 514/10.7
(58) Field of Classification Search ............ None
See application file for complete search history.

(56) References Cited

U.S. PATENT DOCUMENTS 4,866,038 A   9/1989   Hruby et al.

FOREIGN PATENT DOCUMENTS

WO   2006/012667 A1   2/2006
WO   2006/037188 A1   4/2006

OTHER PUBLICATIONS

Definition of analog from http://cancerweb.ncl.ac.uk/omd/about.html, pp. 1-5. Accessed Jul. 7, 2005.*
Photosensitivity from Merck manual, pp. 1-2. Accessed Jan. 16, 2012.*
Ting, W.W., et al., "Practical and experimental consideration of sun protection in dermatology," International Journal of Dermatology, 2003, vol. 42, pp. 505-513.
Luger, T.A., et al., "Role of epidermal cell-derived a-melanocyte stimulating hormone in ultraviolet light mediated local immunosuppression," Ann NY Acad. Sci., 1999, vol. 885, pp. 209-216. (Abstract only).
International Search Report from International Patent Application Publication No. WO2008/025094, dated Oct. 16, 2007.

* cited by examiner

*Primary Examiner* — Julie Ha
(74) *Attorney, Agent, or Firm* — Lisa V. Mueller; Michael Best & Friedrich LLP

(57) ABSTRACT

This invention relates to a method for prophylactic or therapeutic treatment of photodermatoses that are caused or exacerbated by or associated with UVR exposure in a subject, particularly a human subject, which comprises the step of administering to said subject an amount of an alpha-MSH analogue effective to reduce the photosensitivity of the skin of the subject.

4 Claims, 1 Drawing Sheet

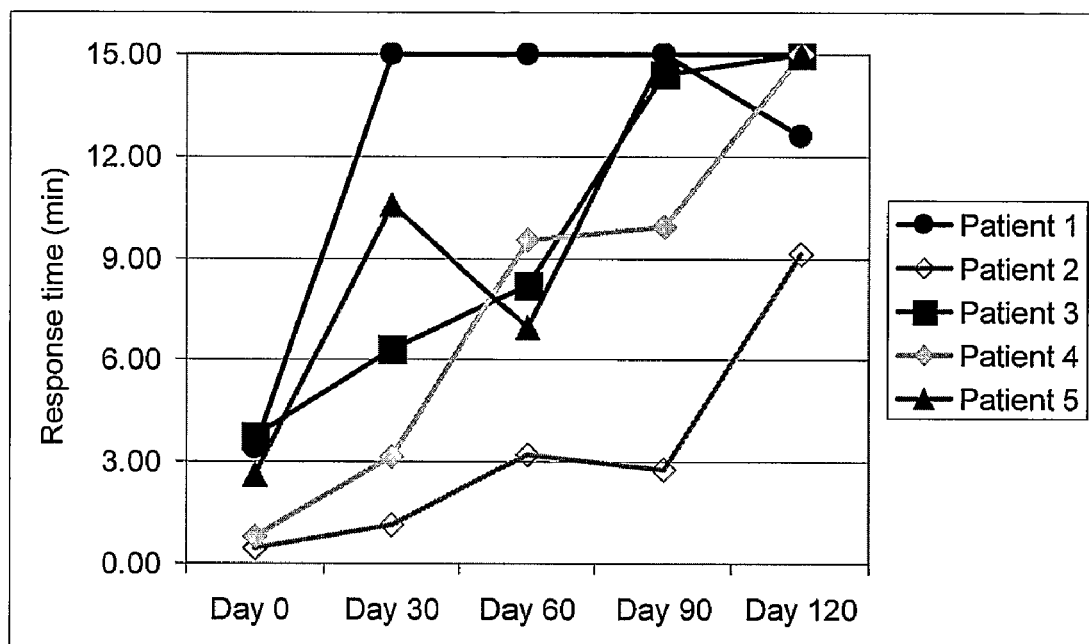

METHOD OF TREATMENT OF PHOTODERMATOSES

RELATED APPLICATIONS

This application is a 371 of PCT Application No. PCT/AU2007/001276, filed Aug. 31, 2007, which claims priority to Australian Patent Application No. 2006904745, filed Aug. 31, 2006, and to Australian Patent Application No. 2007900862, filed Feb. 21, 2007, the contents of all of which are herein incorporated by reference in their entireties.

SEQUENCE LISTING

The instant application contains a Sequence Listing which has been submitted via EFS-Web and is hereby incorporated by reference in its entirety. Said ASCII copy, created on Jan. 12, 2010, is named 0655318.txt, and is 12,551 bytes in size.

FIELD OF THE INVENTION

The present invention relates broadly to a method for prophylactically or therapeutically treating photodermatoses that are associated with photosensitivity of the skin to ultraviolet radiation (UVR).

BACKGROUND

Alpha melanocyte stimulating hormone (alpha-MSH) is released from UVR exposed keratinocytes in human skin following exposure to ultraviolet radiation. It is understood to act on the melanocortin-1-receptors (MC1R) to, exclusively in melanocytes, induce synthesis of the brownish-black melanin pigment. MC1R are expressed on keratinocytes as well as number of other cells including, but not exclusively, immunological cells such as dendritic/Langerhans cells, neutrophils, microglia and monocytes as well as astrocytes, and endothelial cells.

It has previously been disclosed that a super-potent derivative of alpha-MSH, $Nle^4$-D-$Phe^7$-$\alpha$-MSH, can induce melanin synthesis in human volunteers. $Nle^4$-D-$Phe^7$-$\alpha$-MSH contains two amino acid substitutions and is approximately 10 to 1,000-fold more potent than the native hormone at inducing pigmentation in experimental systems such as the frog skin bioassay or in cultured human keratinocytes.

There is a need for methods for treatment or prevention of photodermatoses which include skin reactions to UVR, including by way of example, phototoxicity, photoallergy including actinic dermatitis and solar urticaria, idiopathic reactions including actinic prurigo and polymorphous light eruption, metabolic and nutritional reactions including erythropoietic protoporphyria, DNA-deficient photodermatoses including xeroderma pigmentosum, epidermalysis bullosa, photoexacerbated dermatoses and chronic photodamage.

The present invention provides a method for prophylactically or therapeutically treating photodermatoses by administration of an alpha-MSH analogue.

Bibliographic details of the publications referred to in this specification by reference number are collected at the end of the specification.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein is susceptible to variations and modifications other than those specifically described. It is to be understood that the invention includes all such variations and modifications, the invention also includes all of the steps, features, compositions and compounds referred to or indicated in this specification, individually or collectively, and any and all combinations or any two or more of said steps or features.

SUMMARY OF THE INVENTION

In one aspect, the present invention provides a method for prophylactic or therapeutic treatment of photodermatoses that are caused or exacerbated by or associated with UVR exposure in a subject, particularly a human subject, which comprises the step of administering to said subject an amount of an alpha-MSH analogue effective to reduce the photosensitivity of the skin of the subject.

In another aspect, the present invention provides the use of an alpha-MSH analogue in, or in the manufacture of a medicament for, prophylactic or therapeutic treatment of photodermatoses that are caused or exacerbated by or associated with UVR exposure in a subject, particularly a human subject.

In yet another aspect, the invention provides an agent for use in prophylactic or therapeutic treatment of photodermatoses that are caused or exacerbated by or associated with UVR exposure in a subject, particularly a human subject, comprising an alpha-MSH analogue.

BRIEF DESCRIPTION OF THE DRAWINGS

FIG. 1 shows photoprovocation response times of EPP patients after subcutaneous administration of an implant containing CUV1647 in a sterile polymer excipient. The response time was chosen to be limited to 15 minutes as maximum.

DETAILED DESCRIPTION OF THE INVENTION

Before the present methods are disclosed and described, it is to be understood that the aspects described below are not limited to specific methods or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

By "contacting" is meant an instance of exposure by close physical contact of at least one substance to another substance. For example, contacting can include contacting a substance, such as a pharmacologic agent, with a cell. A cell can be contacted with a test compound, for example, an analogue of alpha-MSH, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the test compound is present at physiologically effective levels or at presumed physiologically effective levels in the medium or extracellular fluid bathing the cell.

The terms "prophylactic treatment", "prevention" or "preventing" mean the administration of an active compound or composition to a subject at risk for an undesirable condition. The condition can include a disease, disorder or reaction, or a predisposition to a disease, disorder or reaction. Prophylactic treatment can range from a reduction in the risk for the condition or of the severity of the condition to the complete prevention of the condition.

The terms "therapeutic treatment" and "treating" mean the administration of an active compound or composition to a subject having an undesirable condition such as a disease, disorder or reaction. Therapeutic treatment can range from reduction in the severity of the condition in the subject to the complete recovery of the subject from the condition.

By "effective amount and time" means a therapeutic amount and time needed to achieve the desired result or results, e.g., preventing or treating photosensitivity associated with UVR exposure in a subject.

By "induce" means initiating a desired response or result that was not present prior to the induction step. The term "induce" also includes the term "potentiate."

By "intermittent" means administering an active compound or composition in a series of discreet doses over a determined period, e.g., a period of sustained release comprising of greater than 24 hours of an alpha-MSH analogue every two months.

The term "potentiate" means sustaining a desired response at the same level prior to the potentiating step or increasing the desired response over a period of time.

The term "melanogenesis" as referred to herein is defined as the ability of a subject to produce melanins by melanin-producing cells, or melanocytes.

The term "epidermal tissue" as referred to herein includes in particular the skin of a subject.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein are methods for prophylactically or therapeutically treating photodermatoses associated with photosensitivity of the skin to UVR exposure.

In one aspect, the invention provides a method for the prophylactic or therapeutical treatment of photodermatoses that are caused or exacerbated by or associated with UVR exposure in a subject, particularly a human subject, which comprises the step of administering to said subject an amount of an alpha-MSH analogue effective to reduce the photosensitivity of the skin of the subject.

Preferably, the alpha-MSH analogue is administered at a level not exceeding 100 ng/ml in the plasma of the subject for a period of at least 24 hours. Preferably also, the administration of the alpha-MSH analogue to the subject is systemic administration, even more preferably intermittent systemic administration.

Preferably, the subject is a human subject.

In another aspect, the present invention provides the use of an alpha-MSH analogue in, or in the manufacture of a medicament for, prophylactic or therapeutic treatment of photodermatoses that are caused or exacerbated by or associated with UVR exposure in a subject, particularly a human subject.

The photodermatoses are diseases or conditions of the skin that are associated with photosensitivity of the skin to UVR. This photosensitivity may arise because of some genetic defect in a subject as in the case of erythropoietic protoporphyria (EPP) and congenital erythropoietic porphyria (CEP) in which porphyrins cause acute photosensitivity (see for example Murphy, 2003; Lecha, 2003; Schneider-Yin et al., 2000; Thunell, 2000). However, other disorders associated with photosensitivity of the skin have also been recognised, including, for example, solar urticaria (SU), (see for example, Roelands, 2003; Dice, 2004; Ferguson, 2003; Rose et al., 2005). Polymorphous light eruption (PLE) is a common sun-induced skin disorder which consists of a rash that is intensely itchy with red blisters, bumps and patches on sun exposed areas of the skin.

The present invention extends to treatment of all such photodermatoses, whether the photosensitivity associated with the condition arises from a genetic defect or not.

The term "alpha-MSH analogue" referred to herein is defined as a derivative of alpha-MSH which exhibits agonist activity for the melanocortin-1 receptor (MC1R), the receptor to which alpha-MSH binds to initiate the production of melanin within a melanocyte. Such derivatives include derivatives in which (i) one or more amino acid residues are deleted from the native alpha-MSH molecule at the N-terminal end, the C-terminal end, or both; and/or (ii) one or more amino acid residues of the native alpha-MSH molecule are replaced by another natural, non-natural or synthetic amino acid residue; and/or (iii) an intramolecular interaction forms as a cyclic derivative.

The use of any alpha-MSH analogue is contemplated in the methods described herein. Several derivatives of α-MSH have been synthesized. In one aspect, the alpha-MSH analogues described in U.S. Pat. Nos. 4,457,864, 4,485,039, 4,866,038, 4,918,055, 5,049,547, 5,674,839, 5,683,981 and 5,714,576, which are herein incorporated by reference for their teachings with respect to alpha-MSH analogues and their synthesis thereof, can be used herein.

In one aspect, the alpha-MSH analogue may be a compound as disclosed in Australian Patent No. 597630, selected from:

(a) compounds of the formula:

```
                                          (SEQ ID NO: 1)
Ac-Ser-Tyr-Ser-M-Gln-His-D-Phe-Arg-Trp-Gly-
    Lys-Pro-Val-NH₂
``` wherein M is Met, Nle or Lys; and
(b) compounds of the formula:

```
                                          (SEQ ID NO: 2)
                 R₁-W-X-Y-Z-R₂
``` wherein
R₁ is Ac-Gly-, Ac-Met-Glu, Ac-Nle-Glu-, or Ac-Tyr-Glu-;
W is -His- or -D-His-;
X is -Phe-, -D-Phe-, -Tyr-, -D-Tyr-, or -(pNO₂)D-Phe⁷-;
Y is -Arg- or -D-Arg-;
Z is -Trp- or -D-Trp-; and
R₂ is —NH₂; -Gly-NH₂; or -Gly-Lys-NH₂.

In another aspect, the alpha-MSH analogue may be selected from cyclic analogues which are disclosed in Australian Patent No. 618733 where an intramolecular interaction (such as a disulfide or other covalent bond) exists (1) between the amino acid residue at position 4 and an amino acid residue at position 10 or 11, and/or (2) between the amino acid residue at position 5 and the amino acid residue at position 10 or 11.

The alpha-MSH analogue may be a linear analogue as disclosed in U.S. Pat. No. 5,674,839 selected from the group consisting of:

```
                                          (SEQ ID NO: 3)
Ac-Ser-Tyr-Ser-Nle-Glu-His-D-Phe-Arg-Trp-Lys-
    Gly-Pro-Val-NH₂

(SEQ ID NO: 4)
Ac-Ser-Tyr-Ser-Nle-Asp-His-D-Phe-Arg-Trp-Lys-
    Gly-Pro-Val-NH₂

(SEQ ID NO: 5)
Ac-Nle-Glu-His-D-Phe-Arg-Trp-Lys-Gly-Pro-Val-NH₂

(SEQ ID NO: 6)
Ac-Nle-Asp-His-D-Phe-Arg-Trp-Lys-Gly-Pro-Val-NH₂

(SEQ ID NO: 7)
Ac-Nle-Asp-His-D-Phe-Arg-Trp-Gly-NH₂

(SEQ ID NO: 8)
Ac-Nle-Glu-His-D-Phe-Arg-Trp-Lys-NH₂

(SEQ ID NO: 9)
Ac-Nle-Asp-His-D-Phe-Arg-Trp-Lys-NH₂
```

```
                                          (SEQ ID NO: 10)
Ac-Nle-Glu-His-D-Phe-Arg-Trp-Orn-NH₂

(SEQ ID NO: 11)
Ac-Nle-Asp-His-D-Phe-Arg-Trp-Orn-NH₂

(SEQ ID NO: 12)
Ac-Nle-Glu-His-D-Phe-Arg-Trp-Dab-NH₂

(SEQ ID NO: 13)
Ac-Nle-Asp-His-D-Phe-Arg-Trp-Dab-NH₂

(SEQ ID NO: 14)
Ac-Nle-Glu-His-D-Phe-Arg-Trp-Dpr-NH₂

(SEQ ID NO: 15)
Ac-Nle-Glu-His-Phe-Arg-Trp-Lys-NH₂

(SEQ ID NO: 16)
Ac-Nle-Asp-His-Phe-Arg-Trp-Lys-NH₂
```

The alpha-MSH analogue may also be a cyclic analogue as disclosed in U.S. Pat. No. 5,674,839, selected from the group consisting of:

(SEQ ID NO: 17)
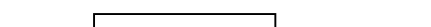
Ac-Nle-Glu-His-D-Phe-Arg-Trp-Lys-Gly-Pro-Val-NH₂

(SEQ ID NO: 18)
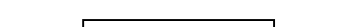
Ac-Nle-Glu-His-D-Phe-Arg-Trp-Lys-NH₂

(SEQ ID NO: 19)
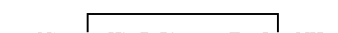
Ac-Nle-Asp-His-D-Phe-Arg-Trp-Lys-NH₂

(SEQ ID NO: 20)
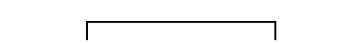
Ac-Nle-Asp-His-D-Phe-Arg-Trp-Orn-NH₂

(SEQ ID NO: 21)
Ac-Nle-Asp-His-D-Phe-Arg-Trp-Dab-NH₂

(SEQ ID NO: 22)
Ac-Nle-Asp-His-D-Phe-Arg-Trp-Dpr-NH₂

(SEQ ID NO: 23)
Ac-Ser-Tyr-Ser-Nle-Asp-His-D-Phe-Arg-Trp-Lys-Gly-Pro-Val-NH₂

(SEQ ID NO: 24)
Ac-Ser-Try-Ser-Nle-Asp-His-D-Phe-Arg-Trp-Lys-NH₂

(SEQ ID NO: 25)
Ac-Tyr-Ser-Nle-Asp-His-D-Phe-Arg-Trp-Lys-NH₂

(SEQ ID NO: 26)
Ac-Ser-Nle-Asp-His-D-Phe-Arg-Trp-Lys-NH₂

(SEQ ID NO: 27)
Ac-Nle-Asp-His-D-Phe-Arg-Trp-Lys-NH₂

(SEQ ID NO: 28)
Ac-Nle-Asp-His-D-Phe-Arg-Trp-Lys-Gly-NH₂

-continued

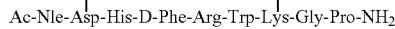
Ac-Nle-Asp-His-D-Phe-Arg-Trp-Lys-Gly-Pro-NH₂ (SEQ ID NO: 29)

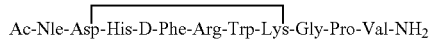
Ac-Nle-Asp-His-D-Phe-Arg-Trp-Lys-Gly-Pro-Val-NH₂ (SEQ ID NO: 30)

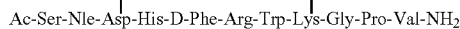
Ac-Ser-Nle-Asp-His-D-Phe-Arg-Trp-Lys-Gly-Pro-Val-NH₂ (SEQ ID NO: 31)

Where referred to herein, Ala=alanine, Arg=arginine, Dab=2,4-diaminobutyric acid, Dpr=2,3-diaminopropionic acid, Glu=glutamic acid, Gly=glycine, His=histidine, Lys=lysine, Met=methionine, Nle=norleucine, Orm=ornithine, Phe=phenylalanine, (pNO₂)Phe=paranitrophenylalanine, Plg=phenylglycine, Pro=proline, Ser=serine, Trp=tryptophan, TrpFor=N¹-formyl-tryptophan, Tyr=tyrosine, Val=valine. All peptides are written with the acyl-terminal end at the left and the amino terminal end to the right; the prefix "D" before an amino acid designates the D-isomer configuration, and unless specifically designated otherwise, all amino acids are in the L-isomer configuration.

In one aspect, the alpha-MSH analogue can be
[D-Phe⁷]-alpha-MSH,
[Nle⁴, D-Phe⁷]-alpha-MSH,
[D-Ser¹, D-Phe⁷]-alpha-MSH,
[D-Tyr², D-Phe⁷]-alpha-MSH,
[D-Ser³, D-Phe⁷]-alpha-MSH,
[D-Met⁴, D-Phe⁷]-alpha-MSH,
[D-Glu⁵, D-Phe⁷]-alpha-MSH,
[D-His⁶, D-Phe⁷]-alpha-MSH,
[D-Phe⁷, D-Arg⁸]-alpha-MSH,
[D-Phe⁷, D-Trp⁹]-alpha-MSH,
[D-Phe⁷, D-Lys¹¹]-alpha-MSH,
[D-Phe-⁷, D-Pro¹²]-alpha-MSH,
[D-Phe⁷, D-Val¹³]-alpha-MSH,
[D-Ser¹, Nle⁴, D-Phe⁷]-alpha-MSH,
[D-Tyr², Nle⁴, D-Phe⁷]-alpha-MSH,
[D-Ser³, Nle⁴, D-Phe⁷]-alpha-MSH,
[Nle⁴, D-Glu⁵, D-Phe⁷]-alpha-MSH,
[Nle⁴, D-His⁶, D-Phe⁷]-alpha-MSH,
[Nle⁴, D-Phe⁷, D-Arg⁸]-alpha-MSH,
[Nle⁴, D-Phe⁷, D-Trp⁹]-alpha-MSH,
[Nle⁴, D-Phe⁷, D-Lys¹¹]-alpha-MSH,
[Nle⁴, D-Phe⁷, D-Pro¹²]-alpha-MSH,
[Nle⁴, D-Phe⁷, D-Val¹³]-alpha-MSH,

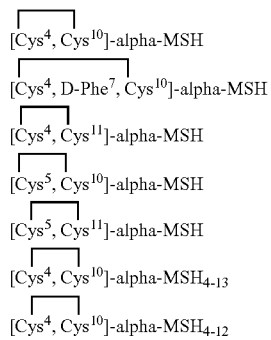

[Nle⁴, D-Phe⁷]-alpha-MSH₄₋₁₀,
[Nle⁴, D-Phe⁷]-alpha-MSH₄₋₁₁,
[D-Phe⁷]-alpha-MSH₅₋₁₁,
[Nle⁴, D-Tyr⁷]-alpha-MSH₄₋₁₁,
[(pNO₂)D-Phe⁷]-alpha-MSH₄₋₁₁,
[Tyr⁴, D-Phe⁷]-alpha-MSH₄₋₁₀,
[Tyr⁴, D-Phe⁷]-alpha-MSH₄₋₁₁,
[Nle⁴]-alpha-MSH₄₋₁₁,
[Nle⁴, (pNO₂)D-Phe⁷]-alpha-MSH₄₋₁₁,
[Nle⁴, D-His⁶]-alpha-MSH₄₋₁₁,
[Nle⁴, D-His⁶, D-Phe⁷]-alpha-MSH₄₋₁₁,
[Nle⁴, D-Arg⁸]-alpha-MSH₄₋₁₁,
[Nle⁴, D-Trp⁹]-alpha-MSH₄₋₁₁,
[Nle⁴, D-Phe⁷, D-Trp⁹]alpha-MSH₄₋₁₁,
[Nle⁴, D-Phe⁷]-alpha-MSH₄₋₉, or
[Nle⁴, D-Phe⁷, D-Trp⁹]-alpha-MSH₄₋₉.

In a further aspect, the alpha-MSH analogue is
[Nle⁴, D-Phe⁷]-alpha-MSH₄₋₁₀,
[Nle⁴, D-Phe⁷]-alpha-MSH₄₋₁₁,
[Nle⁴, D-Phe⁷, D-Trp⁹]-alpha-MSH₄₋₁₁, or
[Nle⁴, D-Phe⁷]-alpha-MSH₄₋₉.

In a particularly preferred aspect, the alpha-MSH analogue is [Nle⁴, D-Phe⁷]-alpha-MSH.

In another aspect, as described above the alpha-MSH analogue may be a truncated derivative of alpha-MSH, including a truncated derivative in which one or more amino acid residues of the truncated native alpha-MSH molecule are replaced by another natural, non-natural or synthetic amino acid residue. Thus, the alpha-MSH analogue may be a truncated derivative such as the tetrapeptide alpha-MSH analogues of the formula:

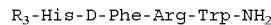
R₃-His-D-Phe-Arg-Trp-NH₂ (SEQ ID NO: 32)

wherein R₃ is Ac, n-pentadecanoyl, or 4-phenylbutyryl; as disclosed by Abdel-Malek et al., (2006).

The alpha-MSH analogue may be administered in a sustained-release delivery system a disclosed in International Patent Application No. PCT/AU2005/000181 (WO 2006/012667), or topically using a transdermal delivery system as disclosed in International Patent Application No. PCT/AU2005/001552 (WO 2006/037188).

It will be appreciated that the actual preferred amounts of the alpha-MSH analogue in a specified case will vary according to the specific compounds being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining doses for prophylactically or therapeutically treating photodermatoses by administration of an amount of an alpha-MSH analogue by the methods described herein. In one aspect, the alpha-MSH analogue is administered in an amount which is effective to prophylactically or therapeutically treat photodermatoses.

Any of the alpha-MSH analogues useful herein can be administered to a subject using a variety of administration or delivery techniques known in the art. It is desirable to maintain low concentrations of the alpha-MSH analogue in the plasma of the subject to induce prophylactically or therapeutically treatment of photodermatoses in the subject. Therefore, the mode of administration will depend upon the subject to be treated and the alpha-MSH analogue selected. In various aspects, the alpha-MSH analogues can be administered orally or parenterally. The term "oral" is used herein to encompass administration of the compounds via the digestive tract. The term "parenteral" is used herein to encompass any route of administration, other than oral administration, by which the alpha-MSH analogue is introduced into the systemic circulation which includes, but is not limited to, intravenous, intramuscular, subcutaneous, intraperitoneal, intradermal, ocular, inhalable, rectal, vaginal, transdermal, topical, buccal, sublingual, or mucosal administration. The term "mucosal" as used herein encompasses the administration of the compounds by methods that employ the mucosa (mucous membranes) of the human body such as, but not limited to, buccal, intranasal, gingival, vaginal, sublingual, pulmonary, or rectal tissue. The term "transdermal" as used herein encompasses the administration of the compounds that go into the skin or go through the skin using formulations such as, but not limited to, transdermal formulations, buccal patches, skin patches, or transdermal patches. The term "topical" as used herein encompasses administration by applying conventional topical preparations such as creams, gels, or solutions for localized percutaneous delivery and/or by solution for systemic and/or localized delivery to areas such as, but not limited to the eye, skin, rectum, and vagina.

In one aspect, delivery systems composed of devices or compositions containing an alpha-MSH analogue can be manufactured that allow for the controlled-release, extended-release, modified-release, sustained-release, pulsatile-release, or programmed-release delivery of the alpha-MSH analogue in order to maintain concentration of the alpha-MSH analogue in the plasma of the subject. Depending on the delivery system or composition of a formulation or route of administration chosen, drugs or active pharmaceutical ingredients can be delivered for hours, weeks, or months following a single administration. Drug-delivery devices include, but are not limited to pumps, needle-free injectors, metered-dose inhalers, and the like. Transdermal compositions with or without penetration enhancers include but are not limited to transdermal patches, microneedles, and transdermal formulations that achieve drug delivery using iontophoresis, sonophoresis, electroporation, thermoporation, perfusion, adsorption and absorption. Other delivery systems include, but are not limited to, biodegradable or non-biodegradable rods or other shaped implants, fibers, microparticles, microspheres, microcapsules, nanospheres, nanocapsules, porous silicon nanoparticles, in situ gelling formulations, in situ bolus forming compositions, quick dissolving tablets and the like, buccal patches, films, tablets, capsules, osmotic pressure driven formulations, liquid filled capsules, liposomes and other lipid based compositions and the like, pegalation and the like, hydrogel formulations, emulsions, microemulsions, and suspensions.

In one aspect, polymeric delivery systems can be microparticles including, but not limited to microspheres, microcapsules, nanospheres and nanoparticles comprising biodegradable polymeric excipients, non-biodegradable polymeric excipients, or mixtures of polymeric excipients thereof, or the polymeric delivery systems can be, but not limited to rods or other various shaped implants, wafers, fibers, films, in situ forming boluses and the like comprising biodegradable polymeric excipients, non-biodegradable polymeric excipients, or mixtures thereof. These systems can be made from a single polymeric excipient or a mixture or blend of two or more polymeric excipients.

A suitable polymeric excipient includes, but is not limited to, a poly(diene) such as poly(butadiene) and the like; a poly(alkene) such as polyethylene, polypropylene, and the like; a poly(acrylic) such as poly(acrylic acid) and the like; a poly(methacrylic) such as poly(methyl methacrylate), a poly(hydroxyethyl methacrylate), and the like; a poly(vinyl ether); a poly(vinyl alcohol); a poly(vinyl ketone); a poly(vinyl halide) such as poly(vinyl chloride) and the like; a poly(vinyl nitrile), a poly(vinyl ester) such as poly(vinyl acetate) and the like; a poly(vinyl pyridine) such as poly(2-vinyl pyridine), poly(5-methyl-2-vinyl pyridine) and the like; a poly(styrene); a poly(carbonate); a poly(ester); a poly(orthoester) including a copolymer; a poly(esteramide); a poly(anhydride); a poly(urethane); a poly(amide); a cellulose ether such as methyl cellulose, hydroxyethyl cellulose, hydroxypropyl methyl cellulose, and the like; a cellulose ester such as cellulose acetate, cellulose acetate phthalate, cellulose acetate butyrate, and the like; a poly(saccharide), a protein, gelatin, starch, gum, a resin, and the like. These materials may be used alone, as physical mixtures (blends), or as co-polymers. Derivatives of any of the polymers listed above are also contemplated.

In one aspect, the polymeric excipient of the delivery system includes a biocompatible, non-biodegradable polymer such as, for example, a silicone, a polyacrylate; a polymer of ethylene-vinyl acetate; an acyl substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; or a blend or copolymer thereof.

In another aspect, the polymeric excipient includes a biocompatible, biodegradable polymer such as, for example, a poly(lactide); a poly(glycolide); a poly(lactide-co-glycolide); a poly(lactic acid); a poly(glycolic acid); a poly(lactic acid-co-glycolic acid); a poly(caprolactone); a poly(orthoester); a poly(phosphazene); a poly(hydroxybutyrate) or a copolymer containing a poly(hydroxybutarate); a poly(lactide-co-caprolactone); a polycarbonate; a polyesteramide; a polyanhydride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, or a blend or copolymer thereof.

In one aspect, the delivery system comprises an implant or rod, wherein the implant or rod comprises a biodegradable polymer, wherein the alpha-MSH analogue is embedded within the implant or rod. In one aspect, the alpha-MSH analogue is encapsulated in an implant or rod composed of poly(lactide-co-glycolide), poly(lactide), poly(glycolide), or a mixture thereof. Lactide/glycolide polymers for drug-delivery formulations are typically made by melt polymerization through the ring opening of lactide and glycolide monomers. Some polymers are available with or without carboxylic acid end groups. When the end group of the poly(lactide-co-glycolide), poly(lactide), or poly(glycolide) is not a carboxylic acid, for example, an ester, then the resultant polymer is referred to herein as blocked or capped. The unblocked polymer, conversely, has a terminal carboxylic group. In one aspect, linear lactide/glycolide polymers are used; however star polymers can be used as well. In certain aspects, high molecular weight polymers can be used for medical devices, for example, to meet strength requirements. In other aspects, low molecular weight polymers can be used for drug-delivery and vaccine delivery products where resorption time and not material strength is as important. The lactide portion of the polymer has an asymmetric carbon. Commercially racemic DL-, L-, and D-polymers are available. The L-polymers are more crystalline and resorb slower than DL-polymers. In addition to copolymers comprising glycolide and DL-lactide or L-lactide, copolymers of L-lactide and DL-lactide are available. Additionally, homopolymers of lactide or glycolide are available.

In the case when the biodegradable polymer is poly(lactide-co-glycolide), poly(lactide), or poly(glycolide), the amount of lactide and glycolide in the polymer can vary. In one aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In one aspect, the biodegradable polymer can be poly(lactide), 85:15 poly(lactide-co-glycolide), 75:25 poly(lactide-co-glycolide), or 65:35 poly(lactide-co-glycolide) where the ratios are mole ratios.

In one aspect, when the biodegradable polymer is poly(lactide-co-glycolide), poly(lactide), or poly(glycolide), the polymer has an intrinsic viscosity of from 0.15 to 1.5 dL/g, 0.25 to 1.5 dL/g, 0.25 to 1.0 dL/g, 0.25 to 0.8 dL/g, 0.25 to 0.6 dL/g, or 0.25 to 0.4 dL/g as measured in chloroform at a concentration of 0.5 g/dL at 30° C.

The amount of alpha-MSH analogue that is encapsulated or incorporated in the biodegradable polymer will vary depending upon the selection of the biodegradable polymer, the encapsulation or incorporation technique, and the amount of alpha-MSH to be delivered to the subject. In one aspect, the amount of alpha-MSH analogue encapsulated in the microcapsule, implant, or rod can be up to 50% by weight of the delivery system. In other aspects, the amount of alpha-MSH analogue encapsulated in the microcapsule, implant, or rod can be from 5 to 60, 10 to 50%, 15 to 40%, or 15 to 30% by weight of the delivery system.

In another aspect, where the alpha-MSH analogue is delivered by another delivery system such as a transdermal formulation, the amount of alpha-MSH analogue in the formulation can be from 0.001 to 10%, or 0.05 to 5% by weight of the formulation.

Other pharmaceutically-acceptable components can be encapsulated or incorporated in the delivery system in combination with the alpha-MSH analogue. For example, the pharmaceutically-acceptable component can include, but is not limited to, a fatty acid, a sugar, a salt, a water-soluble polymer such as polyethylene glycol, a protein, polysaccharide, or carboxymethyl cellulose, a surfactant, a plasticizer, a high- or low-molecular-weight porosigen such as polymer or a salt or sugar, or a hydrophobic low-molecular-weight compound such as cholesterol or a wax. In another aspect, the delivery system comprises an implant or rod, wherein the alpha-MSH analogue is [Nle$^4$, D-Phe$^7$]-alpha-MSH in the amount from 15% to 45% by weight of the implant or rod, wherein the rod or implant comprises poly(lactide) or poly(lactide-co-glycolide) such as, for example, 85:15 poly(lactide-co-glycolide).

Any of the delivery systems described herein can be administered using techniques known in the art. In one aspect, the delivery system can be administered subcutaneously to the subject. In this aspect, the duration of administration can vary depending upon the amount of alpha-MSH analogue that is encapsulated and the biodegradable polymer selected. In one aspect, the delivery system is administered subcutaneously to the subject and releases the alpha-MSH analogue for a period of at least 2, 4, 6, 8, 10 or 12 days. In one aspect, the delivery system releases the alpha-MSH analogue in the subject for up to three months. In various other aspects, the delivery system releases the alpha-MSH analogue in the subject for 10 days, 15 days, 20 days, 25 days, or 30 days.

In one aspect, any of the alpha-MSH analogues can be combined with at least one pharmaceutically-acceptable carrier to produce a pharmaceutical composition. The pharmaceutical compositions can be prepared using techniques known in the art. In one aspect, the composition is prepared by admixing the alpha-MSH analogue with a pharmaceutically-acceptable carrier. The term "admixing" is defined as mixing the two components together so that there is no chemical reaction or physical interaction. The term "admixing" also includes the chemical reaction or physical interaction between the alpha-MSH analogue and the pharmaceutically-acceptable carrier.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, ointments, suppositories, sprays, liquids and powders. Conventional pharmaceutical carriers, aqueous, powder or oily bases, thickeners and the like may be necessary or desirable. The alpha-MSH analogue can be admixed under sterile conditions with a physiologically acceptable carrier and any preservatives, buffers, propellants, or absorption enhancers as may be required or desired. Reference is made to documents cited herein, e.g., U.S. Pat. No. 5,990,091, WO 98/00166, and WO 99/60164, for the preparation of compositions for topical applications, e.g., viscous compositions that can be creams or ointments, as well as compositions for nasal and mucosal administration.

In the case when the composition is administered mucosally, ocularly, intranasally, or by inhalation, the formulation can be in the form of a drop, a spray, an aerosol, or a sustained release format. The spray and the aerosol can be achieved through use of the appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California; Joshi, A., S. Ping and K. J. Himmelstein, Patent Application WO 91/19481). These systems maintain prolonged drug contact with the absorptive surface preventing washout and nonproductive drug loss.

The invention is further described with reference to the following non-limiting Examples which illustrate various embodiments of the invention.

Example 1

Patients who are suffering from photodermatoses and skin diseases have been shown to react to UV-exposure as expressed by various immediate or delayed dermal reactions. Factors such as a family history of photodermatoses, the variance in patients, intensity of the UV-light varying by time of day, and seasonal influence are important factors in the onset of disease. The first step in evaluating a photosensitive patient is based on a directed personal and family history. The morphology of the eruption, phototests, and in some patients, photopatch tests are essential in focusing the diagnosis. Skin biopsies and laboratory investigations, such as antinuclear antibody (ANA) panels and porphyrin profiles, may be required to further confirm the diagnosis.

Photodermatoses can be classified into 5 general categories:
- idiopathic photodermatoses, including polymorphic light eruption (PLE or PMLE), actinic prurigo, hyroa vacciniforme, chronic actinic dermatitis, and solar urticaria;
- photodermatoses which are secondary to exogenous agents, including phototoxic and photoallergic reactions;
- photodermatoses secondary to endogenous agents, mainly the porphyrias;
- photoexacerbated dermatoses, including autoimmune disease, infectious conditions, and nutritional deficiencies; and
- genodermatoses.

Porphyrias, specifically Porphyria Cutanea Tarda, more specifically the Variegate form of Porphyria and most specifically Erythropoietic PhotoPorphyria (EPP), is a genetic disorder in which the impaired ferrochelatase pathway results in the accumulation of the metabolic end product protoporphyrin (PpIX). Accumulation of protoporphyrin in the skin is responsible for cutaneous photosensitivity leading to (i) pain, (ii) swelling, (iii) discrete scarring and (iv) formation of ulcers or lesions. In the presence of light at 410 nm and above, protoporphyrin generates reactive oxygen species resulting in the typical phototoxic reactions. Protoporphyrin is eliminated exclusively via the liver, and when the capacity of the biliary excretion pathway is exceeded, excess protoporphyrin may result in the formation of gallstones or cholestatic liver damage.

In EPP, photodermatoses are most severe and cause unbearable and unsustainable pain and suffering to patients following exposure to UV. Two main clinical manifestations of elevated levels of protoporphyrin are observed in these patients: cutaneous photosensitivity and hepatobiliary disease. Photosensitivity is the most common and usually first presents in early childhood as intolerance to sun-exposure. Patients experience severe burning pain of the skin most often on the face and dorsal sides of the hands. The symptoms may last for several days and may be accompanied by swelling and redness (erythema) on sun or UV exposed areas.

Available treatment modalities and therapeutic agents for patients with EPP are limited. Avoidance of strong sunlight, either from direct exposure or through window glass, and the use of protective clothing is essential to prevent phototoxic reactions. Systemic β-carotene has been shown to be of some benefit in the treatment of EPP although good efficacy data are lacking. The clinical benefits of other treatments such as PUVA, UVB, oral cysteine, cholestyramine and combinations thereof remain to be proven. The most effective measures are use of reflecting sunscreens containing titanium dioxide.

Therapy with an alpha-MSH analogue such as CUV1647, as provided by the present invention reduces the incidence or rate of development of EPP and other related dermatoses.

An open-label study has been carried out in EPP patients with a severe history of photodermatoses exacerbated on the surfaces of their bodies, with a primary objective of determining whether CUV1647 implants can reduce the susceptibility of patients with EPP to provocation with a standardised light source (time to appearance of provoked symptoms). The study was conducted in accordance with the Declaration of Helsinki and its revisions, ICH guidelines for Good Clinical Practice (GCP) governing the conduct of studies, and all applicable local regulations.

Study Procedure

Subjects were recruited from a database of EPP patients. According to the main criteria for entry into the study, eligible subjects were adult male or female patients (aged 18-70 years) with a diagnosis of EPP (confirmed by elevated free protoporphyrin in peripheral erythrocytes and/or ferrochelatase mutation) of sufficient severity that they have requested treatment to alleviate symptoms. Written informed consent was obtained from each patient prior to the performance of any study-specific procedure.

To determine eligibility for entry into the study, patients underwent a screening evaluation prior to the first dose of study drug. Five eligible patients were enrolled (3 male, 2 female) and received CUV1647 (20 mg/implant contained in a poly(D,L-lactide) implant core, giving sustained release of study drug over 10 days on Days 0 and 60. After administration of CUV1647, the patients were contacted the next day for assessment of adverse events and for testing safety. Patients were again contacted one week after implantation to check tolerability of the substance.

The primary objective of the study was to determine if administration of CUV1647 could reduce the susceptibility of EPP patients to standardised light provocation. Secondary endpoints were to determine the effect of CUV1647 on melanin density at specified body sites, to evaluate the number and severity of phototoxic reactions, and the safety by measuring treatment-emergent events.

Results

Photoprovocation was performed with a 300 W Xenon Arc Lamp in a LSH201 Lamp housing (LOT Oriel Gruppe, Darmstadt Germany) equipped with a 385FG03-50(N256) filter (Andover corporation) that suppressed the light below 385 nm and a water filter (LSZ130 LOT) absorbing infrared radiation (White light). For sham exposure a filter (VIS-NIR Interference Filter-model 59415, GlobalSpec, Troy, N.Y.) was used, that restricts the irradiation to wavelength 630±10 nm (red light). The distance from the skin was fixated at 3.5 cm, whilst a circular surface area of 3.8 cm$^2$ was irradiated by a focal bundle of light serving as source of provocation. The irradiation power at the skin surface was determined before and after photoprovocation by a NIST traceable Radiometer/Photometer Model IL1400A, equipped with a SCS2820 detector (International Light, Newbury, Mass.). The recorded power with white light was in the range of 132±13 mW/cm$^2$.

Photoprovocation was performed before administration (day 0) and again on day 30, 60, 90 and 120. The increase in photoprovocation times—defined as time to first intolerable pain experienced following irradiation—varied over all 5 patients from 173% to 2124%. The results are summarized in FIG. 1. Tolerated radiation dose increased likewise in all patients, the range being between 218 and 2511 percent compared to baseline values. The difference in times endured to first pain, at day 30, 60 90 and 120 proved to be statistically significant (p=0.0070; Friedman test). The difference in tolerated irradiation dose likewise was statistically significant (p=0.0151; Friedman test).

Melanin density: Melanin density (MD) was recorded by spectrophotometry (Minolta Chromameter 2500d). MD increased during the first 30 days after administration at all tested sites with one exception in one patient. The change in MD as measured on days 0, 30, 60, 90 and 120 (measured at 6 anatomical sites) was statistically significant (p=0.0043). One arbitrary MD unit corresponds with about one level in the classification of Fitzpatrick skin types. The increase in pigmentation induced darkening of the dermis with natural appearance that was well appreciated by patients.

Phototoxic reactions: Phototoxic reactions and sun exposure times were recorded from diaries of the patients. Three patients reported phototoxic reactions within the first 4 days after application of the first dose of CUV1647. Thereafter, only sporadic, low grade phototoxic reactions were recorded. Nonetheless, the recorded maximum daily sun exposure times of the patients corresponded to 1800, 1200, 300 and 75% of their sun light tolerance as reported by the respective patients before treatment. The total sun exposure times were above 4000 min during 4 months in 3 patients.

Conclusions:

The intended primary endpoint of this study was met, as all 5 EPP patients increased their tolerance to artificial light provocation after treatment with CUV1647, a finding that was highly significant. The clinical relevance of this positive effect of CUV1647 on the main EPP symptom was underlined by a nearly total lack of phototoxicity experienced by the patients in their daily lives as recorded in diary notes and in anecdotal information. Expectedly, CUV1647 increased significantly melanin pigmentation in the skin of the patients. As a further result of the study, it was shown that CUV1647 was well tolerated by the patients, and no serious drug-related event was recorded.

Example 2

Polymorphous Light Eruption (PLE) or sun poisoning is a severe debilitating skin disorder with an incidence of 10-20% in the general population. It is characterised by frequent and severe outbreaks of burning sensations, blisters and vesicles in individuals exposed to sunlight. Patients with PLE often learn to live with the disease, and only the severe patients (approximately 10% of the total sufferers) present the disease to dermatologists. Currently, there is no efficacious therapy for PLE. These individuals suffer from recurrent symptoms from spring through summer, shun the outdoors and lead an isolated life.

A double-blind, randomized, placebo-controlled Phase II study was carried out to evaluate the safety and efficacy of a single subcutaneous implant of CUV1647 in subjects suffering from recurrent PLE.

Study Procedure.

Male and female subjects aged between 18 and 70 years diagnosed with PLE-like symptoms were enrolled in the study, and 26 subjects were divided into two groups (13 administered CUV1647 and 13 administered a placebo).

A single subcutaneous administration of an implant containing 20 mg (±5%) of CUV1647 in a sterile polymer excipient (DL-Lactide) was given to each study subject in the active treatment arm. the implant was designed to release the entire dose of study medication in the first 10 days and was biodegradable thereafter. Implants were delivered subcutaneously to the abdomen using a trocar cannula obturator via a small incision. After implantation, the incision was sutured if required.

A single subcutaneous administration of an implant containing matching placebo in a sterile polymer excipient (DL-Lactide) was given to each study subject in the placebo-control arm. Implants were delivered subcutaneously to the abdomen using a trocar cannula obturator via a small incision. After implantation, the incision was sutured if required.

Efficacy

PLE Severity

Severity scores for PLE symptoms from subject's diaries were calculated as the sum of the severity (1+mild, 2=moderate and 3=severe) recorded for each body site (face, arms, legs, etc.) and morphological symptom (hives, blisters, burning, etc.). This resulted in an overall severity score for the subject for that day. The daily severity scores were totaled for each 30 day period to obtain a monthly severity score which gave an indication of the severity of the disease experienced during that month.

PLE Episodes

The number of episodes of PLE for each subject was calculated as the total number of times the overall daily severity score exceeded 7 for at least two consecutive days.

Quality of Life

Change in life quality was assessed using the Dermatological Life Quality Index.

Skin Reflectance Measurements

Change in skin darkening was determined by melanin density (MD), skin luminescence (L*) and by blue/yellow colour hue (B*-value) from skin reflectance measurements (CIELAB standard observer response).

Safety:

Safety was assessed by:

Type and incidence of treatment emergent adverse events.

Physical examination changes.

Changes in weight, temperature, blood pressure and heart rate.

Changes in clinical chemistry, haematology and urinalysis parameters.

Efficacy Results:

There were no statistically significant differences between treatment groups in monthly severity scores at any time point. Median total monthly severity scores were lower in the CUV1647 group compared to the placebo group at Day 30 (4.5 versus 9.0), but higher at other time points. Median monthly severity scores by calendar month were lower in the CUV1647 group compared to the placebo group during the summer months of December and January. The number of episodes of PLE to Day 90 was not statistically significantly different in the CUV1647 group compared to the placebo group.

There was a statistically significant difference in the use of systemic corticosteroids between treatment groups with one (7.7%) subject in the CUV1647 group and eight (61.5%) subjects in the placebo group using this form of steroid treatment (p value=0.0112 Fisher's Exact test).

There was no significant difference in the use of topical corticosteroids (dermatological preparations) between treatment groups (p value=1.000 Fisher's Exact test) with four 30.8%) using topical steroids in the CUV1647 group and three (23.1%) in the placebo group.

Discussion

The increased requirement for steroid-rescue medication in the placebo group highlighted the greater severity of PLE symptoms in the placebo recipients compared to the active group. The use of steroids is associated with a variety of undesirable side effects caused by the short-acting disturbance of the natural endocrine (hormonal) system. The reduced requirement for steroids as maintenance medication in PLE patients is an important outcome for this trial.

CUV1647 recipients also experienced fewer PLE episodes than those on placebo (mean 0.38 versus 0.85 per patient).

Safety and tolerability of systemically administered CUV1647 proved to be good and no major safety concerns were identified.

Example 3

Solar Urticaria (SU) is a severely debilitating and disabling disease following exposure to sun or UV-light. Patients with a known history of SU have acute or delayed dermal exacerbations. There is a known variance in patients; intensity of the UV-light varying by time of day, and seasonal influence are important factors in the onset of disease (see for example Meola et al., 1993; Roelandts, 2000; Monfrecola et al., 2000; Uetsu et al.; Watanabe et al, 1999).

Solar urticaria is an uncommon disorder characterized by pruritus, erythema and whealing commencing within minutes of exposure to ultraviolet (UV) and visible light, and generally resolves in a few hours. The interval between exposure to the sun and development of skin lesions, as well as the duration of individual lesions, can be helpful in the diagnosis. For example, lesions of solar urticaria usually occur within minutes of sun exposure and last for less than 24 hours.

There are several indications for phototesting, firstly to establish the presence of a photosensitivity disorder, and secondly to provide information regarding the action spectrum of the dermatoses. Provocative light testing allows reproduction of the eruption of the disease, often in a localized area of the skin and in milder form. Phototesting involves the assessment of dermal response and reaction time to UVA, UVB, and visible light. Specifically, tests are conducted to assess the MED to UVA, UVB, and an urticarial response to visible light along the relevant wavelengths.

A placebo-controlled study is carried out using CUV1647 in patients with confirmed SU. A primary objective of the study is to determine whether CUV1647 implants can reduce the susceptibility of patients with SU to provocation with a standardised light source (time to appearance of provoked symptoms). The study is conducted in accordance with the Declaration of Helsinki and its revisions, ICH guidelines for Good Clinical Practice (GCP) governing the conduct of studies, and all applicable local regulations.

Subjects are recruited from a database of SU patients. According to the main criteria for entry into the study, eligible subjects are adult male or female patients (aged 18-70 years) with Fitzpatrick Skin Type I-IV and a diagnosis of SU (confirmed by phototesting) of sufficient severity that they have requested treatment to alleviate symptoms. Written informed consent is obtained from each patient prior to the performance of any study-specific procedure.

To determine eligibility for entry into the study, patients undergo a screening evaluation at −14 days prior to the first dose of study drug. An additional screening visit at −7 days occurs if results from the provocation tests at Day −14 are inconclusive. Eligible patients receive one dose of CUV1647 (20 mg/implant contained in a poly(D,L-lactide) implant core, giving sustained release of study drug over 10 to 15 days) subcutaneously on Day 0. Placebo implants contain poly(D,L-lactide) polymer excipient but no active drug.

At the screening visit (Day −14 and possibly Day −7) and again on Days 7, 30, 60, 90 and 120, patients are phototested and a "time taken to develop provoked symptoms" determined on a small part of the patient's midback. Melanin density (measured spectrophotometrically) is determined at all clinic visits while the number and severity of phototoxic reactions and the use of rescue medication is recorded in patient diaries. Quality of life is measured at screening and again on Day 90. Participants visit the clinic on Days 7, 30, 60, 90 and 120 for assessments of adverse events and for safety bloods. In addition, on Day 1 (approximately 24 hours after administration of the implant) a blood sample is taken for drug level measurements and urinalysis.

The criteria for evaluation of the study are efficacy analyses and safety analyses:

Efficacy Analyses:

The primary efficacy endpoint of this study is the time taken for the development of symptoms provoked during phototesting. The primary efficacy analysis will compare the "time to appearance of provoked symptoms" before (Day −14 and possibly Day −7) and after CUV1647 treatment (Days 7, 30, 60, 90 and 120) in each patient by an appropriate statistical method. $H_0$: there is no difference in "time taken to develop provoked symptoms" before and after treatment.

Secondary efficacy endpoints include:

the number and severity of phototoxic reactions (to be compared with documented historical data) and the use of rescue medication, the level of melanin density in the skin as measured by a spectrophotometer (analysis will compare changes in melanin density from baseline to the post-treatment assessments at Days 7, 30, 60, 90 and 120), Safety Analyses:

The number of participants with treatment-emergent adverse events will be summarised by MedDRA preferred term and body system for each treatment group. Treatment-emergent events will be further summarised by intensity, seriousness, outcome and relationship to study drug. Participants who prematurely terminate treatment due to adverse events related to study medication will be summarised. Clinical laboratory data will be summarised for each treatment group.

References

1. Dice, J. P., Physical urticaria. *Immunol. Allerg. Clin. N. Am.*, (2004), 24:225-246.
2. Ferguson, J. Diagnosis and treatment of the common idiopathic photodermatoses. *Aust. J. Dermatol.* (2003), 44:90-96.
3. Lecha, M. Erythropoietic protoporphyria. *Photodermatol. Photoimmunol. Photomed.* (2003), 16:57-64.
4. Meola, T., Lim, H. W., Soter, N. A. Evaluation of the photosensitive patient. In: Lim H W, Solter N A, eds. *Clinical photomedicine*. New York: Marcel Dekker, (1993).
5. Monfrecola, G., Masturzo E., Riccardo A. M., Balato, F., Ayala, F., Di Costanzo, M. P. Solar urticaria: A report on 57 cases. *Am J Contact Dermatitis* (2000), 11:89-94.
6. Murphy, G. M. Diagnosis and management of the erythropoietic porphyrias. *Dermatologic Therapy* (2003), 16:57-64.
7. Roelandts, R. The diagnosis of photosensitivity. *Arch. Dermatol.* (2000), 136:1152-1157.
8. Roelandts, R. Diagnosis and treatment of solar urticaria. *Dermatologic Therapy*. (2003), 16:52-56.

9. Rose, R. F., Bhushan, M., King, C. M., Rhodes, L. E., Solar angioedema: an uncommonly recognized condition? *Photodermatol. Photoimmunol. Photomed.* (2005), 21:226-228.
10. Schneider-Yin, X., Gouya, L., Meier-Weinand, A., Deybach, J.-C., Minder, E. I. New insights into the pathogenesis of erythropoietic protoporphyria and their impact on patient care. *Eur. J. Pediatr.* (2000), 159:719-725.
11. Thunnell, S., Harper, P., Brun, A. Porphyrins, porphyrin metabolism and porphyrias, IV. Pathophysiology of erythropoietic protoporphyria—diagnosis, care and monitoring of the patient. *Scand. J. Clin. Lab. Invest.* (2000), 60:581-604.
12. Uetsu, N., Miyauchi-Hashimoto, H., Okamoto, H., Horio, T. The clinical and photobiological characteristics of solar urticaria in 40 patients. *Br. J. Derm.* 14:32-38.
13. Watanabe, M., Matsunaga, Y., Katayama, I. Solar urticaria: a consideration of the mechanism of inhibition spectra. *Dermatology* (1999), 198.
14. Abdel-Malek, S, Kadekavo, A C, Kavanagh, R J et al., Melanoma prevention strategy based on using tetrapeptide α-MSH analogs that protect human melanocytes from UV-induced DNA damage and cytotoxicity. *FASEB J* (2006); 20: E888-E896.

The invention claimed is:

1. A method for treating a human subject suffering from photodermatoses that are caused or exacerbated by or associated with ultraviolet radiation (UVR) exposure which comprises the step of administering to said subject an amount of [$Nle^4$, $D-Phe^7$]-alpha-melanocyte stimulating hormone (alpha-MSH) effective to reduce the photosensitivity of the skin of the subject.

2. The method of claim 1, wherein the photodermatosis is erythropoietic photoporphyria (EPP).

3. The method of claim 1, wherein the photodermatosis is solar urticaria (SU).

4. The method of claim 1, wherein the photodermatosis is polymorphous light eruption (PLE).

* * * * *

UNITED STATES PATENT AND TRADEMARK OFFICE

(12)     CERTIFICATE EXTENDING PATENT TERM
              UNDER 35 U.S.C. § 156

| | | | |
|---|---|---|---|
| (68) | PATENT NO. | : | 8,334,265 |
| (45) | ISSUED | : | December 18, 2012 |
| (75) | INVENTOR | : | Phillippe Wolgen |
| (73) | PATENT OWNER | : | Clinuvel Pharmaceuticals Limited |
| (95) | PRODUCT | : | SCENESSE® (afamelanotide acetate) |

This is to certify that an application under 35 U.S.C. § 156 has been filed in the United States Patent and Trademark Office, requesting extension of the term of U.S. Patent No. 8,334,265 based upon the regulatory review of the product SCENESSE® (afamelanotide acetate) by the Food and Drug Administration. According to United States Patent and Trademark Office records, the original expiration date of the patent as of the date of issuance of this certificate is March 11, 2029. Because it appears that the requirements of the law have been met, this certificate extends the term of the patent for the period of

(94)                              1,411 days subject to the payment of maintenance fees as provided by law, with all rights pertaining thereto as provided by 35 U.S.C. § 156.

I have caused the seal of the United States Patent and Trademark Office to be affixed this 25th day of May 2023.

*Kathi Vidal*

Katherine K. Vidal
Under Secretary of Commerce for Intellectual Property and
Director of the United States Patent and Trademark Office

```
                         SEQUENCE LISTING

<160> NUMBER OF SEQ ID NOS: 32

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Met, Nle or Lys
<220> FEATURE:
<221> NAME/KEY: MOD_RES
<222> LOCATION: (7)..(7)
<223> OTHER INFORMATION: D-Phe

<400> SEQUENCE: 1

Ser Tyr Ser Xaa Gln His Phe Arg Trp Gly Lys Pro Val
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Met, Nle or Tyr
<220> FEATURE:
<221> NAME/KEY: MOD_RES
<222> LOCATION: (2)..(2)
<223> OTHER INFORMATION: May or may not be present
<220> FEATURE:
<221> NAME/KEY: MOD_RES
<222> LOCATION: (3)..(3)
<223> OTHER INFORMATION: His or D-His
<220> FEATURE:
<221> NAME/KEY: MOD_RES
<222> LOCATION: (4)..(4)
<223> OTHER INFORMATION: Phe, D-Phe, Tyr, D-Tyr or paranitro-D-Phe
<220> FEATURE:
<221> NAME/KEY: MOD_RES
<222> LOCATION: (5)..(5)
<223> OTHER INFORMATION: Arg or D-Arg
<220> FEATURE:
<221> NAME/KEY: MOD_RES
<222> LOCATION: (6)..(6)
<223> OTHER INFORMATION: Trp or D-Trp
<220> FEATURE:
<221> NAME/KEY: MOD_RES
<222> LOCATION: (7)..(7)
<223> OTHER INFORMATION: May or my not be present
<220> FEATURE:
```

```
<221> NAME/KEY: MOD_RES
<222> LOCATION: (8)..(8)
<223> OTHER INFORMATION: May or my not be present

<400> SEQUENCE: 2

Xaa Glu His Xaa Arg Trp Gly Lys
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe

<400> SEQUENCE: 3

Ser Tyr Ser Xaa Glu His Phe Arg Trp Lys Gly Pro Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe

<400> SEQUENCE: 4

Ser Tyr Ser Xaa Asp His Phe Arg Trp Lys Gly Pro Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 5

Xaa Glu His Phe Arg Trp Lys Gly Pro Val
1               5                   10

<210> SEQ ID NO 6
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 6

Xaa Asp His Phe Arg Trp Lys Gly Pro Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 7

Xaa Asp His Phe Arg Trp Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 8

Xaa Glu His Phe Arg Trp Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 9
```

Xaa Asp His Phe Arg Trp Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn

<400> SEQUENCE: 10

Xaa Glu His Phe Arg Trp Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn

<400> SEQUENCE: 11

Xaa Asp His Phe Arg Trp Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab

<400> SEQUENCE: 12

Xaa Glu His Phe Arg Trp Xaa
1               5

```
<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab

<400> SEQUENCE: 13

Xaa Asp His Phe Arg Trp Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dpr

<400> SEQUENCE: 14

Xaa Glu His Phe Arg Trp Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle

<400> SEQUENCE: 15

Xaa Glu His Phe Arg Trp Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Nle

<400> SEQUENCE: 16

Xaa Asp His Phe Arg Trp Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 17

Xaa Glu His Phe Arg Trp Lys Gly Pro Val
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 18

Xaa Glu His Phe Arg Trp Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
```

```
<223> OTHER INFORMATION: D-Phe

<400> SEQUENCE: 19

Xaa Asp His Phe Arg Trp Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn

<400> SEQUENCE: 20

Xaa Asp His Phe Arg Trp Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab

<400> SEQUENCE: 21

Xaa Asp His Phe Arg Trp Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
```

```
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dpr

<400> SEQUENCE: 22

Xaa Asp His Phe Arg Trp Xaa
1               5

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: misc_feature
<222> LOCATION: (5)..(10)
<223> OTHER INFORMATION: cyclic peptide
<220> FEATURE:
<221> NAME/KEY: MOD_RES
<222> LOCATION: (7)..(7)
<223> OTHER INFORMATION: D-Phe

<400> SEQUENCE: 23

Ser Tyr Ser Xaa Asp His Phe Arg Trp Lys Gly Pro Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: misc_feature
<222> LOCATION: (5)..(10)
<223> OTHER INFORMATION: cyclic peptide
<220> FEATURE:
<221> NAME/KEY: MOD_RES
<222> LOCATION: (7)..(7)
<223> OTHER INFORMATION: D-Phe

<400> SEQUENCE: 24

Ser Tyr Ser Xaa Asp His Xaa Arg Trp Lys
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: Nle
<220> FEATURE:
<221> NAME/KEY: misc_feature
<222> LOCATION: (4)..(9)
<223> OTHER INFORMATION: cyclic peptide
<220> FEATURE:
<221> NAME/KEY: MOD_RES
<222> LOCATION: (6)..(6)
<223> OTHER INFORMATION: D-Phe

<400> SEQUENCE: 25

Tyr Ser Xaa Asp His Phe Arg Trp Lys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: misc_feature
<222> LOCATION: (3)..(8)
<223> OTHER INFORMATION: cyclic peptide
<220> FEATURE:
<221> NAME/KEY: MOD_RES
<222> LOCATION: (5)..(5)
<223> OTHER INFORMATION: D-Phe

<400> SEQUENCE: 26

Ser Xaa Asp His Phe Arg Trp Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 27

Xaa Asp His Phe Arg Tyr Lys
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
```

```
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 28

Xaa Asp His Phe Arg Trp Lys Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 29

Xaa Asp His Phe Arg Trp Lys Gly Pro
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: cyclic peptide
<220> FEATURE:
<221> NAME/KEY: MOD_RES
<222> LOCATION: (4)..(4)
<223> OTHER INFORMATION: D-Phe

<400> SEQUENCE: 30

Xaa Asp His Phe Arg Trp Lys Gly Pro Val
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: misc_feature
<222> LOCATION: (3)..(8)
```

```
<223> OTHER INFORMATION: cyclic peptide
<220> FEATURE:
<221> NAME/KEY: MOD_RES
<222> LOCATION: (5)..(5)
<223> OTHER INFORMATION: D-Phe

<400> SEQUENCE: 31

Ser Xaa Asp His Phe Arg Trp Lys Gly Pro Val
1               5                   10

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Phe

<400> SEQUENCE: 32

His Phe Arg Trp
1
```